United States Patent [19]
Shanmugasundaram et al.

[11] Patent Number: 5,980,902
[45] Date of Patent: Nov. 9, 1999

[54] COMPOSITIONS FOR TREATING AND PREVENTING DIABETES, IMPAIRED GLUCOSE TOLERANCE AND RELATED SYMPTOMS, AND METHODS FOR PREPARING AND USING SUCH COMPOSITIONS

[75] Inventors: Edayatimangalam Raja Bhavani Shanmugasundaram; Kalathinkal Radha Shanmugasundaram, both of Chennai, India; Rolland Hébert, Seattle, Wash.; Sohail Malik, Seattle, Wash.; Michael Baker, Seattle, Wash.

[73] Assignee: Pharma Terra, Inc., Bellevue, Wash.

[21] Appl. No.: 09/048,966

[22] Filed: Mar. 26, 1998

[51] Int. Cl.$^6$ .................................................. A01N 65/00
[52] U.S. Cl. ........................................................ 424/195.1
[58] Field of Search ........................................... 424/195.1

[56] References Cited

U.S. PATENT DOCUMENTS

| | | |
|---|---|---|
| 4,761,286 | 8/1988 | Hiji . |
| 4,912,089 | 3/1990 | Hiji . |
| 5,612,039 | 3/1997 | Policappelli et al. . |
| 5,730,988 | 3/1998 | Womack ............................ 424/195.1 |

OTHER PUBLICATIONS

Shanmugasundaram et al., Enzyme Changes and Gluscose Utilisation in Diabetic Rabbits: The Effect of *Gymnema Sylvestre*, R.Br., *Journal of Ethnopharmacology* 7, pp. 205–234, 1983.

Murakami et al., New Hypoglycemic Constituents in "Gymnemic Acid" from *Gymnema Sylvestre*, *Chem. Pharm. Bull* 44(2), pp. 469–471, 1996.

Liu et al., Isolation and Structure Elucidation of Gymnemic Acids, Antisweet Principles of *Gymnema sylvestre*, *Chem, Pharm. Bull.* 40(6), pp. 1366–1375, 1992.

Rao et al., Constituents from *Gymnema sylvestre* Leaves VIII: Isolation Chemistry, and Derivatives of Gymnemagenin and Gymnestrogenin, *Journal of Pharmaceutical Sciences* 60(2), pp. 190–192, 1971.

Sinsheimer et al., Constituents from *Gymnema sylvestre* Leaves V: Isolation and Preliminary Characterization of the Gymnemic Acids, *Journal of Pharmaceutical Sciences* 59(5), pp. 622–628, 1970.

Rathi et al., Studies on Protein–bound Polysaccharide Components & Glycosaminoglycans in Experimental Diabetes–Effect of *Gymnema sylvestre*, R. Br., *Indian Jrnl Experimental Biol* 19, pp. 715–721, 1981.

Shanmugasundaram et al., Possible Regeneration of the Islets of Langerhans in Streptozotocin–diabetic Rats Given *Gymnema Sylvestre* Leaf Extracts, *Journal of Ethnopharmacology* 30, pp. 265–279, 1990.

Sinsheimer et al., Constituents from *Gymnema sylvestre* Leaves VI: Acylated Genins of the Gymnemic Acids–Isolation and Preliminary Characterization, *Jrnl of Pharmaceutical Sciences* 59(5), pp. 629–632, 1970.

Shanmugasundaram et al., Use of *Gymnema Sylvestre* Leaf Extract in the Control of Blood Glucose in Insulin–dependent Diabetes Mellitus, *Journal of Ethnopharmacology* 30, pp. 281–294, 1990.

Baskaran et al., Antidiabetic Effect of a Leaf Extract from *Gymnema Sylvestre* in Non–insulin–dependent Diabetes Mellitus, *Journal of Ethnopharmacology* 30, pp. 295–305, 1990.

*Primary Examiner*—Herbert J. Lilling
*Attorney, Agent, or Firm*—Ann W. Speckman; Janet Sleath

[57] ABSTRACT

Compositions derived from *Gymnema sylvestre* leaf materials are disclosed. Methods for isolating such compositions are also disclosed. The compositions may be administered orally, intravenously, subcutaneously or transdermally and are useful for treating patients having diabetes, impaired glucose tolerance, and various conditions associated with or symptoms of diabetes. Additionally, the compositions reduce polydipsia, polyuria and polyphagia, regenerate the pancreatic islets of Langerhans, including beta cells, increase endogenous insulin, lipase and amylase levels, increase production of proinsulin and c-peptide, and lower blood lipids and triglycerides and free fatty acids.

10 Claims, 1 Drawing Sheet

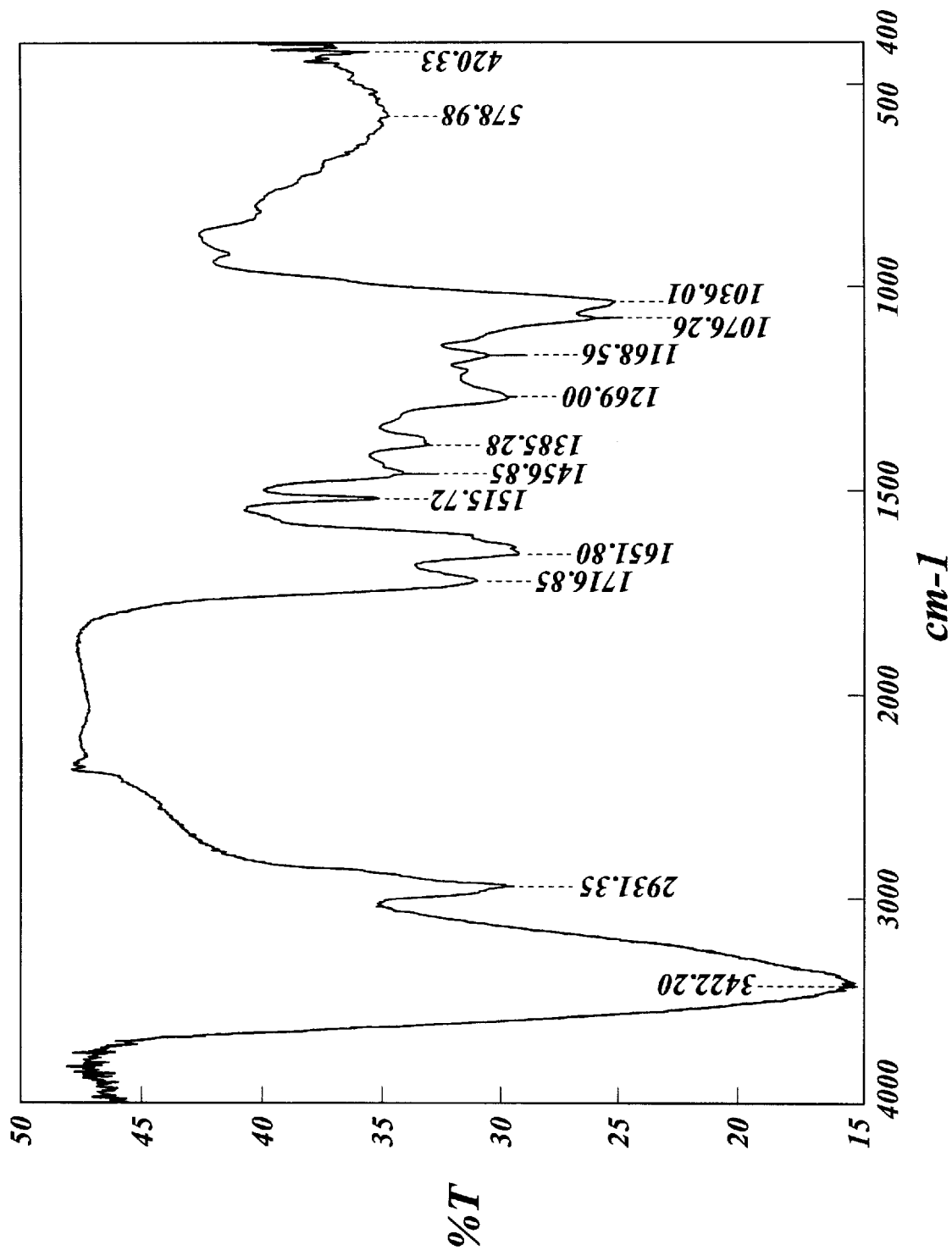

COMPOSITIONS FOR TREATING AND PREVENTING DIABETES, IMPAIRED GLUCOSE TOLERANCE AND RELATED SYMPTOMS, AND METHODS FOR PREPARING AND USING SUCH COMPOSITIONS

TECHNICAL FIELD

The present invention relates generally to compositions derived from certain plant materials, specifically *Gymnema sylvestre* leaf materials, and the treatment of types 1 and 2 diabetes, impaired glucose tolerance, hyperlipidemia, elevated triglyceride levels, elevated free fatty acid levels, and reduced levels of insulin, c-peptide, amylase and lipase using the compositions. Extraction techniques and compositions isolated using those extraction techniques are disclosed. The compositions of the present invention stimulate the regeneration of pancreatic islets and, more preferably, beta cells responsible for the production of insulin.

BACKGROUND OF THE INVENTION

One of the classical clinical symptoms of diabetes is increased blood glucose (hyperglycemia), which may be related to polyuria, polydipsia, polyphagia, weight loss, and blurred vision. The long term complications of untreated or ineffectively treated diabetes include retinopathy, nephropathy, and peripheral neuropathy. Diabetic patients have an increased risk of cardiovascular disease and stroke.

Most diabetic patients fall into one of two categories, based on the mechanism of the pathology. Type 1 diabetics suffer from an absolute deficiency of insulin secretion. The insulin deficiency may be related to an autoimmune process destroying the beta cells of the pancreas. Type 2 diabetics, which comprise 90–95% of all diabetic patients, suffer from insulin resistance. In type 2 diabetics, the insulin resistance may be coupled with the inability of the pancreas to adequately respond with sufficient insulin to compensate for the resistance. In both types of diabetes, the failure of the pancreas to provide an appropriate level of insulin secretion results in the disease. New case reports of type 2 diabetes appear to be increasing at an alarming rate in several Western countries and in developing countries as well. In the United States, for example, it is estimated that approximately five per cent of the adult population suffers from some form of diabetic condition, with the rate of newly diagnosed patients increasing at about 6 per cent per year, or approximately 600,000 new cases each year. The treatment and management of type 2 diabetes requires special dietary measures and, often, the use of a pharmaceutical hypoglycemic agent.

An additional, not yet well defined patient population exhibits preclinical symptoms of diabetic conditions, such as impaired glucose tolerance (IGT). IGT is a condition in which plasma glucose levels during an oral glucose tolerance test are above normal, but below those considered as diagnostic for diabetes. This population is estimated to be in the range of 20 to 22 million people in the United States and remains untreated at this time. Edelman SV: Impaired glucose tolerance: a precursor of type 2 or a separate disease entity in itself? Diabetes News 26:1–5, 1995.

There are currently four chemically distinct families of oral hypoglycemic agents used in the management of type 2 diabetes. The first family of agents, the biguanides, primarily suppress excessive hepatic glucose production. The second family, the sulfonylureas, primarily stimulate the pancreas to secrete insulin. Various sulfonylurea agents are presently sold under approximately 100 different brand names. Sulfonylureas, however, fail to control hypoglycemia on initial use in approximately 30 to 40 percent of new cases (primary failures). In an additional 1 to 5 percent of the new cases, sulfonylurea agents eventually lose their effectiveness (secondary failures). The third family consists of alpha glucosidase inhibitors, which delay the absorption of carbohydrates in the small intestine, thus improving postprandial glucose values. The thiazolidinediones are the fourth and newest class of anti-diabetic agents to be approved by the FDA for the treatment of type 2 diabetes. Thiazolidinediones modulate peripheral insulin resistance in skeletal muscle without stimulating insulin secretion. They also, to a lesser degree, reduce excessive hepatic glucose production. All of these oral hypoglycemic agents have undesirable, and potentially serious, side effects.

There are many natural products which appear to exhibit hypoglycemic activity.

These products are generally plants or plant-derived compounds, usually in the form of a crude extract. It is estimated that more than 200 species of plants exhibit hypoglycemic properties, including many common plants, such as immature bean pods, olive leaves, potatoes, wheat, celery, blackbeny leaves, sugar beets, and the leaves and roots of bananas. Farnsworth and Segelman, Tile Till 57:52–55, 1971. Natural hypoglycemic agents have also been isolated, for example, from the leaves of *Aloe Aboraescens Var Natalis* (Hikino et al, Int. J. Crude Drug Res. 24:183–186, 1986) and from the roots of *Oryza sativa* (Hikino et al, Planta Med. 490–492, 1986).

The seeds of *Eugenia jambolana*, a plant found in India, appear to exhibit hypoglycemic activity comparable to that of chlorpropamide, as determined by effects on cathepsin B (Bansal et al, Indian J. Biochem. Biophysic. 18:377, 1981). Further, it has been reported that *Salvia lavandulifolia* possess a slight hypoglycemic activity that is independent of the effects of insulin (Jimenez et al, Planta Med. 1:260–262, 1986). Other folklore remedies, including tea made from herbs such as *Allofylus edulis* (Barboza et al, Plantas que Curan 1985), *Daucus carota* and *Cantharanthus roseus*, have been sold for the control of diabetes in South American or Southeast Asian countries.

The leaves of *Gymnema sylvestre*, an herb belonging to the Asclepiadaceae family, have been used by traditional medical practitioners of India to treat diabetic conditions for several centuries. *Gymnema sylvestre* has also been studied for its anti-sweet properties, for its ability to inhibit small intestine absorption of glucose, and for its ability to suppress increases in blood glucose levels following glucose administration. In the early 1980's, Shanmugasundaram et al showed that the administration of a dried leaf powder of *Gymnema sylvestre* helped regulate the blood sugar of alloxan diabetic rabbits. Journal of Ethnopharmacology, 7 (1983) pp. 205–234. The authors speculated that the dried leaf caused an increase in insulin output by the already existing beta cells.

In the Indian Journal of Experimental Biology, Vol 19, August 1981, pp 715–721, Shanmugasundaram et al describe an extract of *Gymnema sylvestre*, GS2, and its hypoglycemic activity at one tenth the dose of the dried leaves of Gymnema sylvestre. At that time, the authors attributed the effect of the extract GS2 to the increased availability of insulin and to the facilitation of metabolites in insulin-dependent processes. In a series of articles published in the Journal of Ethnopharmacology in 1990, Shanmugasundaram et al. demonstrated that additional extracts from the leaves of *Gymnema sylvestre*, denominated GS3 and GS4, were able to increase the islet number and beta cell number in diabetic rats. GS4 treatment resulted in a significant reduction in blood glucose, glycosylated hemoglobin and glycosylated plasma proteins, as well as decreases in lipid levels. Both extracts, GS3, and GS4, when administered orally to streptozotocin-induced diabetic rats, caused fasting blood glucose levels to return to normal.

Others have reported in the scientific literature hypoglycemic gymnemic acid constituents from *Gymnema sylvestre* (Murakami et al, Liu et al, Rao et al, Sinsheimer et al). These authors generally report on the ability of the gymnemic acid constituents to inhibit glucose absorption in the small intestine, but have not observed any effect of such compositions on pancreatic tissues.

U.S. Pat. No. 4,761,286 discloses the use of an extract of *Gymnema sylvestre* to inhibit intestinal glucose absorption, thereby decreasing the amount of caloric intake and preventing obesity. This patent discloses that the amount of glucose absorbed will be substantially less than otherwise anticipated when an extract of *Gymnema sylvestre* is added to the foodstuff. U.S. Pat. No. 4,912,089 discloses that a purified extract of *Gymnema sylvestre* inhibits the production of a polysaccharide which is important in the production of plaque implicated in the production of dental caries. This patent teaches the use of purified gymnemic acid as a method of preventing dental caries and does not disclose its use in the prevention or treatment of diabetes. U.S. Pat. No. 5,612,039 discloses adding a dry extract of leaves of *Gymnema sylvestre* to a weight loss composition, but does not discuss the treatment or prevention of diabetes.

An ideal medication for the treatment and prevention of diabetes would be one which would incorporate the following characteristics: ability to stimulate regeneration of pancreatic islets and beta cells responsible for insulin production and to increase c-peptide levels; ability to modulate the autoimmune destruction of the cells responsible for insulin production; ability to correct the dislipidemia associated with diabetes; ability to decrease insulin resistance; and few or no serious side effects. None of the pharmaceutical compositions for treating diabetes meet all of these criterion.

Existing pharmaceutical oral hypoglycemic agents produce inconsistent clinical results, as well as frequent severe side effects. There is a need in the art for safe and effective oral hypoglycemic agents that provide the clinician with a wider range of options for preventing, treating and managing diabetes. In addition, there is a pressing need for an oral hypoglycemic agent which reverses the loss of functional pancreatic islet cells, including beta cells, responsible for insulin synthesis by stimulating the regeneration of these islet cells, including the beta cells, in patients who suffer from type 1 or type 2 diabetes, as well as IGT.

SUMMARY OF THE INVENTION

The present invention provides oral hypoglycemic agents comprising an extract of the leaves of *Gymnema sylvestre*. These compositions and their analogs and derivatives are effective for treatment and prevention of type 1 and type 2 diabetes and impaired glucose tolerance. Methods for the preparation of biologically active extracts of *Gymnema sylvestre* are also disclosed. The compositions of the present invention are also useful for treating hyperlipidemic, elevated triglyceride and free fatty acid conditions resulting from diabetes, modulating the autoimmune reaction responsible for the destruction of the pancreatic islet and beta cells, and increasing the endogenous levels of insulin, c-peptide, amylase and lipase. The compositions of the present invention may be used to treat humans and other warm-blooded animals. Treatment protocols are also disclosed.

BRIEF DESCRIPTION OF THE DRAWING

FIG. 1 shows an FTIR spectrum for one of the extracts from *Gymnema sylvestre* of the present invention identified as GSHAN.

DETAILED DESCRIPTION OF THE INVENTION

The compositions of the present invention include extracts from *Gymnema sylvestre* leaves, as well as analogs and derivatives of those extracts. Such compositions regenerate the pancreatic islets and beta cells and are preferably administered to humans and other warm-blooded animals suffering from type 1 or type 2 diabetes, IGT, or a variety of symptoms of or conditions related to diabetes or IGT. The compositions of the present invention may also be used for treating hyperlipidemia, elevated triglyceride levels, elevated free fatty acid conditions, and reduced levels of insulin, c-peptide, amylase and lipase.

Compositions of the present invention were originally produced from the leaves of the plant *Gymnema sylvestre*. Certain results have previously been reported for compositions derived from *Gymnema sylvestre* leaf material consisting of: (1) a dried leaf powder; (2) an alcohol-water extract of the leaves that was distilled under vacuum and freeze-dried (GS-2); an extract collected as residue from a 50% ethanol/steam extraction that was subsequently filtered, concentrated under vacuum and acidified to pH 3 (GS-3); and an extract purified as described above for GS-3, but additionally dissolved in 0.1 N NaOH and reprecipitated with acid (GS-4).

A preferred extraction technique of the present invention involves fragmenting dried leaves of *Gymnema sylvestre* by gently pounding them, followed by steeping them in an aqueous solution of one or more high polarity organic solvents for at least 24 hours. Such organic solvents may be selected from methanol, propanol, butanol, and amyl alcohol, and a combination of at least two such solvents is preferred. The organic solvent or combination is preferably in an aqueous solution, with the organic solvent constituents comprising at least about 5% v/v, and preferably about 10–30% v/v in the aqueous solution. An especially preferred aqueous alcohol solution for the extraction technique of the present invention comprises propanol/butanol/amyl alcohol, 15–20% v/v. The leaves are preferably steeped in the aqueous alcohol solution for at least 24 hours, more preferably for at least four or five days, at a temperature of from about 10 to 25° C., more preferably from about 15 to 20° C. The extract may then be concentrated, e.g., by evaporation. A salt, such as NaCl, is preferably added to the concentrated extract and the extract is acidified to a pH of about 3.0 or below. Mineral acid is a preferred acidification agent. The water soluble fraction is discarded, and the precipitate is washed. The purified fraction may be dried and used at this stage or, preferably, additional purification techniques may be employed. According to preferred embodiments, the washed precipitate is dissolved in a mild basic solution, such as a saturated solution of sodium bicarbonate, followed by acidification to a pH of about 3.0 or below with an acid such as mineral acid. Again, the water soluble fraction is discarded, the precipitate is washed and dried.

A composition that was used experimentally, designated GSHAN, was prepared as follows. Leaves of *Gymnema* sylvestre were dried, pounded gently to fragment without pulverizing, and were steeped in an aqueous solution of propanol/butanol/amyl alcohol (15–20% v/v) at 15–20° C. for eight to ten days. The extract was concentrated by evaporation. Sodium chloride was added to make the salt concentration 10% and it was acidified with mineral acid to pH 3.0. The water soluble fraction was discarded. The precipitate thus obtained was washed to remove salt and excessive acid. The precipitate was then dissolved in a saturated solution of sodium carbonate. The solution was acidified with mineral acid to pH 3.0, and the water soluble fraction was discarded. The precipitate was filtered and washed with water and dried at room temperature (8% yield). After each step of acidification, water soluble components were completely removed from the mixture, thus leaving only a specific fraction which was insoluble in water at this pH. The double acidification process was used to obtain a specific extract which was only soluble at higher pH. This process also assured complete removal of water soluble components from the extract at the acidic pH.

The Fourier Transform Infrared (FITR) spectrum of the GSHAN composition isolated as described above is shown in FIG. 1. The spectrum was recorded in solid potassium bromide (KBr) using a Perkin-Elmer 1720 spectrophotometer.

Analogs and derivatives of compositions of the present invention include compositions, active constituents, and the like, derived from various fractions or subfractions of *Gymnema sylvestre* preparations, other natural sources, or produced synthetically, that exhibit substantially the same activity as the compositions of the present invention.

Compositions of the present invention may be administered to humans and other warm-blooded animals for the purposes discussed above. Such compositions may be delivered orally, intravenously, subcutaneously or transdermally. Suitable delivery systems are well known in the art. Compositions for use in such treatment methods comprise an effective amount of an extract of *Gymnema sylvestre* or an analog or derivative thereof, in combination with a physiologically acceptable carrier or diluent. Suitable carriers include fillers, binders, excipients and similar materials. Suitable diluents include alcohol, water, physiological saline, and mixtures thereof.

Daily dosages of compositions of the present invention may vary depending on the condition of the patient, the patient's health history and other medications, and the like. In general, dosages of compositions of the present invention, including GSHAN in a dried, powder form, are administered to human patients at dosage levels of approximately 5 mg to 20 grams per day, and more preferably at dosage levels of approximately 150 mg to 1.5 grams per day. Treatment protocols may involve a single daily dosage, or may involve equally divided doses throughout the day. For example, daily treatment with a 750 mg dose of GSHAN may be administered in a single oral administration, or in multiple doses administered at two or more times during the day. The dosage level, as well as the preferred treatment regimen depends upon the individual patient and the patient's response. The optimum dosage for each patient may be determined by monitoring the patient's blood glucose level. In general, patients would begin treatment upon a diagnosis of impaired glucose tolerance or type 1 or 2 diabetes, and continue until normal blood glucose levels are achieved.

Compositions of the present invention may also be administered to reduce symptomatic conditions associated with diabetes in a patient, such as polydipsia, polyuria and polyphagia, to regenerate the pancreatic islets of Langerhans, including beta cells, responsible for the synthesis of insulin, to increase endogenous insulin, lipase and amylase levels in a patient, to increase production of proinsulin and c-peptide, to lower blood lipids and triglycerides, and to simultaneously lower blood free fatty acid levels. The compositions of the present invention may also be used to treat the condition of impaired glucose tolerance.

Compositions of the present invention also lower blood triglyceride and lipid levels in patients who suffer from diabetes and who are therefore at increased risk for cardiovascular disease. This obviates the need to administer an additional cholesterol lowering medication in this patient population. Compositions of the present invention also provide a means to simultaneously lower free fatty acid levels in blood which, when elevated, may play an important role in the pathogenesis of diabetes in predisposed individuals by impairing peripheral glucose utilization and by promoting an overproduction of hepatic glucose. Moreover, compositions of the present invention effectively modulate the autoimmune response in type I diabetic patients in whom newly formed insulin producing cells would otherwise be destroyed.

The following examples describe various experimental systems and data and are offered by way of illustration, and not by way of limitation.

EXAMPLE 1

Diabetes was induced in rats, followed by treatment with the GSHAN preparation for a three week treatment period. The treatment group demonstrated significantly reduced fasting blood glucose levels, increased pancreatic amylase and lipase levels, and dramatically increased the number of pancreatic islets and beta cells.

Male albino rats weighing from 120–150 g were used. All animals were screened for detection of abnormalities in blood glucose by subjecting them to an oral glucose tolerance test. Diabetes was induced in overnight fasted rats by intravenous injection of 55 mg/kg streptozotocin using a 5% solution of freshly prepared streptozotocin in 0.1 M citrate buffer (pH 4.5). Control rats received citrate buffer only. Fasting blood glucose was measured and glucosuria was detected in all the animals seven days after streptozotocin administration. All animals were given powdered food and water ad libitum.

Five weeks (35 days) after the injection of citrate buffer (normal) or streptozotocin (diabetic), diabetic animals were administered GSHAN, while the other half remained untreated for comparison. The dosage used was 20 mg/day/rat. The powdered GSHAN extract was mixed with 3 grams of powdered food and moistened with water to make a bolus which the rats ate in the mornings. On day 56, animals were sacrificed and pancreatic tissue was harvested.

Each animal was sacrificed by decapitation and the whole pancreas perfused with formalin and removed immediately together with the spleen. The total pancreatic weight was recorded. The three regions of the pancreas, that is, duodenal (head), gastric (body) and spleen (tail), were dissected according to the specifications of Jaffe, F. A. (1951) A quantitative study of the islets of Langerhans in the rabbit, Anatomie Recurie 111, 109–121. The tissue samples were cut into smaller fragments and fixed separately in Bouin's fluid for 24 hours. The segments were dehydrated with ethanol and embedded in paraffin-wax (560° C.). Serial sections (5 um) were taken and stained with chrome-haematoxylin and phloxin according to Gomori (1941). One hundred serial sections were studied for the number of islets and beta cell content in each one of the three regions of the pancreas for each rat. Beta cells stain deep purple and photographs were taken with green filter to obtain maximum contrast. The number of rats for which histological studies were made was 10 in each group.

Morphometric studies were made using stereological procedures according to Wiebel and Elias (1967) using a reticule. The reticule was mounted along the focal plane of the eye piece, and consisted of 100 squares. At 400× magnification, the area covered by the 100 squares was 0.0625 mm$^2$. The area covered by the section and diameters of the islets and beta cells was measured by counting the number of squares in the reticule occupied by the structures. With the thickness of the sections at 5 um, the volume of the section and islets was arrived at to express the percentage endocrine tissue.

The fasting blood glucose, pancreatic amylase and pancreatic lipase levels, averaged for each test population, are shown in the Table below:

| Test Population | Fasting Blood Glucose mg/dL | Pancreatic amylase IU/ml protein | Pancreatic lipase IU/ml protein |
|---|---|---|---|
| Initial levels, diabetic rats | 218 | 109 | 13 |
| Final levels, Diabetic treated rats | 74 | 675 | 26 |
| Final levels, Diabetic untreated rats | 220 | 98 | 15 |
| Control | 76 | 700 | 28 |

Treatment with GSHAN resulted in a dramatic reduction in fasting blood glucose levels, and dramatic increases in pancreatic amylast and lipase levels. The diabetic rats treated with GSHAN for three weeks nearly achieved fasting blood glucose, pancreatic amylase and pancreatic lipase levels of the non-diabetic, control rats.

The mean number of islets of Langerhans and the number of beta cells/islet in the control, treated diabetic and untreated diabetic rats in the duodenal, gastric and splenic areas of the pancreas following three weeks of treatment with GSHAN were also measured. The results are shown in the Table, below:

| Test Population | Duodenal Pancreas | | Gastric Pancreas | | Splenic Pancreas | |
|---|---|---|---|---|---|---|
| | No. islets | Beta cells/islet | No. islets | Beta cells/islet | No. islets | Beta cells/islet |
| Control | 49 | 250 | 108 | 115 | 89 | 640 |
| Diabetics, treated | 59 | 160 | 38 | 91 | 84 | 328 |
| Diabetics, untreated | 24 | 82 | 0 | 0 | 33 | 147 |

The untreated diabetic rats had significant declines in the number of islets and the number of beta cells per islet in all areas of the pancreas. The treated diabetic rats showed significant increases in the number of islets and the number of beta cells per islet in all areas of the pancreas.

EXAMPLE 2

Six patients diagnosed with type 1 diabetes were administered 1 capsule of GSHAN (200 mg) three times a day along with their insulin. The following table shows, for each patient, the age and gender and length of type 1 diabetes diagnosis, the daily dosage of insulin at the beginning of the GSHAN treatment, as well as the daily insulin dosage following 3 months of treatment with GSHAN, fasting blood glucose levels at 0, 3 and 6 months following treatment, as well as glycosylated hemoglobin levels at 0, 3 and 6 months following GSHAN therapy.

| Patient | Age/Sex | DM, yrs | insulin U/day | | fasting blood glucose mg/dL | | | Hb A1c % | | |
|---|---|---|---|---|---|---|---|---|---|---|
| | | | 0 m | 3 m | 0 m | 3 m | 6 m | 0 m | 3 m | 6 m |
| 1 | 14 M | 6 | 80 | 60 | 225 | 180 | 165 | 14.6 | 13.2 | 10.5 |
| 2 | 8 M | 6 | 50 | 50 | 175 | 150 | 130 | 11.6 | 10.2 | 9.8 |
| 3 | 23 F | 3 | 60 | 60 | 300 | 210 | 170 | 12.2 | 10.8 | 10.2 |
| 4 | 42 M | 25 | 80 | 70 | 16 | 150 | 130 | 10.8 | 9.6 | 8.5 |
| 5 | 38 M | 15 | 80 | 80 | 305 | 215 | 200 | 14.8 | 12.1 | 10.5 |
| 6 | 20 F | ½ | 20 | 0 | 175 | 120 | 95 | 12.1 | 10.8 | 9.5 |

Half of the patients treated were able to reduce their daily insulin dosage during treatment with GSHAN. In fact, patient 6, who had been diagnosed with type 1 diabetes for only six months, was able to eliminate insulin administration altogether following three months of treatment with GSHAN. All patients experienced significant reductions in fasting blood glucose and glycosylated hemoglobin levels during treatment with GSHAN, which are indicative of more effective glucose metabolism.

EXAMPLE 3

Six patients diagnosed with type 1 diabetes were administered 1 capsule of GSHAN (200 mg) three times a day along with their insulin for a four month period. The following table shows the effect of GSHAN on cholesterol, triglycerides (TG), free fatty acids (FFA), blood urea nitrogen (BUN), hemoglobin (Hgb) and c-peptide levels and compares the pre-treatment and treatment levels with normal levels. These results are averaged for the six patients. Significant reductions in cholesterol, triglyceride, free fatty acid and blood urea nitrogen were observed. C-peptide levels increased significantly during GSHAN therapy, indicating an increase in the production of endogenous insulin in type 1 diabetic patients. (Mean+/− standard deviation)

| | cholesterol mg/dL | TG mg/dL | FFA mg/dL | BUN mg/dL | blood Hgb % | c-peptide pmole/ml |
|---|---|---|---|---|---|---|
| Initial | 245 +/− 25 | 175 +/− 21 | 89 +/− 15 | 25 +/− 5 | 16 +/− 1 | 0.10 +/− .05 |
| Final | 225 +/− 18 | 188 +/− 18 | 72 +/− 10 | 21 +/− 5 | 14 +/− 2 | 0.20 +/− .02 |
| Normal | 210 +/− 15 | 105 +/− 10 | 53 +/− 05 | 18 +/− 5 | 15 +/− 2 | 0.27 +/− .02 |

EXAMPLE 4

Six patients diagnosed with type 2 diabetes were administered 1 capsule of GSHAN (200 mg) three times a day along with their other hypoglycemic drugs for a treatment period of four months. The following table shows, for each patient, the age and gender and length of time of type I diabetes diagnosis, the fasting blood glucose levels at 0, 2 and 4 months following treatment, any glycosylated hemoglobin levels at 0, 2 and 4 months following GSHAN therapy. Most patients were able to decrease their other hypoglycemic drugs while on GSHAN therapy.

| Patient | age/sex | duration of DM in yrs | fasting blood glucose mg/dL | | | Hb A1C % | | |
|---|---|---|---|---|---|---|---|---|
| | | | 0 m | 2 m | 4 m | 0 m | 2 m | 4 m |
| 1 | 48 M | 6 | 160 | 140 | 120 | 9.6 | 8.4 | 8.2 |
| 2 | 52 M | 20 | 180 | 160 | 150 | 10.2 | 9.4 | 9.2 |
| 3 | 44 M | 2 | 180 | 140 | 120 | 9.2 | 8.2 | 8.0 |
| 4 | 56 M | 2 | 160 | 120 | 105 | 8.2 | 7.0 | 7.2 |
| 5 | 48 F | 13 | 235 | 210 | 195 | 12.5 | 11.2 | 10.2 |
| 6 | 55 F | 7 | 200 | 180 | 165 | 12.0 | 10.6 | 9.5 |

EXAMPLE 5

Six patients diagnosed with type 2 diabetes were administered 1 capsule of GSHAN (200 mg) three times a day along with their other hypoglycemic drugs for a four month period. The following table shows the effect of GSHAN on cholesterol, triglycerides (TG), free fatty acids(FFA), blood urea nitrogen (BUN), hemoglobin (Hgb), uric acid and postprandial insulin levels. (Mean+/−standard deviation) Significant reductions in cholesterol, triglyceride, free fatty acid and blood urea nitrogen were observed, and were accompanied by an increase in postprandial insulin levels. Results are shown in the table below, and initial and final treatment levels are compared to normal levels.

| | cholesterol mg/dL | TG mg/dL | FFA mg/dL | BUN mg/dL | blood Hgb % | uric acid mg/dL | insulin* IU/ml |
|---|---|---|---|---|---|---|---|
| initial | 260 +/− 18 | 175 +/− 15 | 80 +/− 9 | 24 +/− 5 | 15.2 +/− .8 | 3.6 +/− 0.6 | 55 +/− 6 |
| final | 232 +/− 2.1 | 136 +/− 18 | 64 +/− 8 | 20 +/− 3 | 14.6 +/− .6 | 3.1 +/− .4 | 72 +/− 8 |
| normal | 212 +/− 13 | 103 +/− 15 | 54 +/− 5 | 19 +/− 3 | 15 +/− .8 | 2.5 +/− .4 | 89 +/− 6 |

*post prandial serum insulin levels.

EXAMPLE 6

Six patients diagnosed with impaired glucose tolerance (IGT) based on glucose tolerance tests were administered 1 capsule of GSHAN (200 mg) three times a day for 4 months. The age and gender of each of the patients and the fasting blood glucose levels at 0, 2 and 4 months following treatment with GSHAN are shown in the table below. Treatment with GSHAN resulted in significant reductions in fasting blood glucose levels in all cases.

| Patient | age/sex | fasting blood glucose mg/dL | | |
|---|---|---|---|---|
| | | 0 m | 2 m | 4 m |
| 1 | 50 M | 130 | 112 | 87 |
| 2 | 65 M | 123 | 83 | 80 |
| 3 | 55 M | 136 | 124 | 108 |
| 4 | 61 M | 140 | 120 | 90 |
| 5 | 58 F | 133 | 122 | 106 |
| 6 | 65 F | 129 | 118 | 84 |

We claim:

1. A method for treating diabetic patients, comprising administering a composition isolated from the leaves of *Gymnema sylvestre* by:
   fragrmenting dried leaves of *Gymnema sylvestre* to produce fragmented, dried leaves;
   steeping the fragmented, dried leaves in an aqueous solution comprising one or more high polarity organic solvents for at least 24 hours to produce an extract;
   acidifying the extract to a pH of about 3.0 or below to produce a first acidified extract; and
   discarding a water soluble fraction of the first acidified extract and collecting the precipitate.

2. A method for treating human diabetic patients according to claim 1, comprising administering the composition at a daily dosage of between about 5 mg and 20 grams.

3. A method for treating human diabetic patients according to claim 2, comprising administering the composition in a single daily, oral dosage of about 750 mg.

4. A method for treating impaired glucose tolerance, comprising administering a composition isolated from the leaves of *Gymnema sylvestre* by:
   fragmenting dried leaves of *Gymnema sylvestre* to produce fragmented, dried leaves;
   steeping the fragmented, dried leaves in an aqueous solution comprising one or more high polarity organic solvents for at least 24 hours to produce an extract;
   acidifying the extract to a pH of about 3.0 or below to produce a first acidified extract; and
   discarding a water soluble fraction of the first acidified extract and collecting the precipitate.

5. A method for regenerating the pancreatic islets of Langerhans, comprising administering a composition isolated from the leaves of *Gymnema sylvestre* by:
   fragmenting dried leaves of *Gymnema sylvestre* to produce fragmented, dried leaves;
   steeping the fragmented, dried leaves in an aqueous solution comprising one or more high polarity organic solvents for at least 24 hours to produce an extract;
   acidifying the extract to a pH of about 3.0 or below to produce a first acidified extract; and
   discarding a water soluble fraction of the first acidified extract and collecting the precipitate.

6. A method for regenerating the pancreatic beta cells, comprising administering a composition isolated from the leaves of *Gymnema sylvestre* by:
   fragmenting dried leaves of *Gymnema sylvestre* to produce fragmented, dried leaves;
   steeping the fragmented, dried leaves in an aqueous solution comprising one or more high polarity organic solvents for at least 24 hours to produce an extract;
   acidifying the extract to a pH of about 3.0 or below to produce a first acidified extract; and
   discarding a water soluble fraction of the first acidified extract and collecting the precipitate.

7. A method for increasing endogenous insulin levels in a patient, comprising administering a composition isolated from the leaves of *Gymnema sylvestre* by:
   fragmenting dried leaves of *Gymnema sylvestre* to produce fragmented, dried leaves;
   steeping the fragmented, dried leaves in an aqueous solution comprising one or more high polarity organic solvents for at least 24 hours to produce an extract;
   acidifying the extract to a pH of about 3.0 or below to produce a first acidified extract; and discarding a water soluble fraction of the first acidified extract and collecting the precipitate.

8. A method for increasing the production of proinsulin in a patient, comprising administering a composition isolated from the leaves of *Gymnema sylvestre* by:

fragmenting dried leaves of *Gymnema sylvestre* to produce fragmented, dried leaves;

steeping the fragmented, dried leaves in an aqueous solution comprising one or more high polarity organic solvents for at least 24 hours to produce an extract;

acidifying the extract to a pH of about 3.0 or below to produce a first acidified extract; and discarding a water soluble fraction of the first acidified extract and collecting the precipitate.

9. A method of one of claims 1, 4, 5, 6, 7 and 8, wherein the one or more high polarity organic solvents is selected from the group consisting of: methanol; propanol; butanol; amyl alcohol; and combinations thereof.

10. A method of one of claims 1, 4, 5, 6, 7 and 8, wherein the one or more high polarity organic solvents is a combination of at least two alcohols.

* * * * *